United States Patent
Fridez et al.

(10) Patent No.: US 11,241,530 B1
(45) Date of Patent: Feb. 8, 2022

(54) INSULIN PATCH PUMP HAVING PHOTOPLETHYSMOGRAPHY MODULE

(71) Applicant: AMF Medical SA, Ecublens (CH)

(72) Inventors: Pierre Fridez, Froideville (CH); Laurent Mosimann, Commugny (CH); Antoine Barraud, Lonay (CH)

(73) Assignee: AMF Medical SA, Ecublens (CH)

( * ) Notice: Subject to any disclaimer, the term of this patent is extended or adjusted under 35 U.S.C. 154(b) by 0 days.

(21) Appl. No.: 17/102,334

(22) Filed: Nov. 23, 2020

(51) Int. Cl.
*A61M 5/142* (2006.01)
*A61M 5/172* (2006.01)
*A61B 5/024* (2006.01)

(52) U.S. Cl.
CPC ..... *A61M 5/14248* (2013.01); *A61B 5/02416* (2013.01); *A61M 5/1723* (2013.01); *A61M 2005/14208* (2013.01); *A61M 2005/14252* (2013.01); *A61M 2205/3327* (2013.01); *A61M 2205/583* (2013.01); *A61M 2205/587* (2013.01)

(58) Field of Classification Search
CPC .......... A61M 5/14244; A61M 5/14248; A61M 5/1723; A61M 2005/14208; A61M 2005/14252; A61M 2205/3327; A61M 2205/583; A61M 2205/587; A61B 5/02416

See application file for complete search history.

(56) References Cited

U.S. PATENT DOCUMENTS

| | | |
|---|---|---|
| 2,412,397 A | 12/1946 | Harper |
| 3,609,069 A | 9/1971 | Martinelli |
| 4,042,153 A | 8/1977 | Callahan et al. |
| 4,199,307 A | 4/1980 | Jassawalla |
| 4,218,416 A | 8/1980 | Gokcen |
| 4,273,121 A | 6/1981 | Jassawalla |
| 4,290,346 A | 9/1981 | Bujan |
| 4,493,704 A | 1/1985 | Beard et al. |
| 4,934,372 A | 6/1990 | Corenman et al. |
| 5,088,522 A | 2/1992 | Rath et al. |
| 5,137,023 A | 8/1992 | Mendelson et al. |
| 5,252,044 A | 10/1993 | Raines et al. |

(Continued)

FOREIGN PATENT DOCUMENTS

DE 102013111800 A1 4/2015
EP 0721358 A1 7/1996
(Continued)

OTHER PUBLICATIONS

"Osram"—Light is wearable—Health Monitoring and Fitness Tracking</i>. Flyer posted online Jan. 22, 2015. file:///C:/Users/jponton/Desktop/Osram_676865_Flyer_Health_Monitoring_and_Fitness_Tracking_2016_(GB).pdf (Year: 2015).*

(Continued)

*Primary Examiner* — James D Ponton
(74) *Attorney, Agent, or Firm* — Eversheds Sutherland (US) LLP; Nicola A. Pisano; Christopher C. Bolten

(57) ABSTRACT

A body-worn medication delivery pump having a patch form factor is provided that includes an integrated plethysmographic module that employs a photoplethysmographic multi-chip package disposed in a frame designed to maintain contact with a wearer's skin during motion, and reduces cross-talk and ingress of stray light, a controller of the pump programmed to adjust its medication delivery algorithms responsive to outputs of the plethysmographic module.

20 Claims, 3 Drawing Sheets

(56) References Cited

U.S. PATENT DOCUMENTS

| | | | |
|---|---|---|---|
| 5,637,095 A | 6/1997 | Nason et al. |
| 5,851,197 A | 12/1998 | Marano et al. |
| 5,964,583 A | 10/1999 | Danby |
| 6,093,172 A | 7/2000 | Funderburk et al. |
| 6,165,151 A | 12/2000 | Weiner |
| 6,293,925 B1 | 9/2001 | Safabash et al. |
| 6,607,509 B2 | 8/2003 | Bobroff et al. |
| 6,723,077 B2 | 4/2004 | Pickup et al. |
| 6,830,562 B2 | 12/2004 | Mogensen et al. |
| 6,881,043 B2 | 4/2005 | Barak |
| 7,137,964 B2 | 11/2006 | Flaherty |
| 7,204,823 B2 | 4/2007 | Estes et al. |
| 7,315,753 B2 | 1/2008 | Baker, Jr. et al. |
| 7,329,239 B2 | 2/2008 | Safabash et al. |
| 7,356,364 B1 | 4/2008 | Bullock et al. |
| 7,879,023 B2 | 2/2011 | Wood, Jr. |
| 7,879,026 B2 | 2/2011 | Estes et al. |
| 8,152,771 B2 | 4/2012 | Mogensen et al. |
| 8,657,807 B2 | 2/2014 | Blomquist |
| 9,517,024 B2 | 12/2016 | Kiani et al. |
| 9,610,018 B2 | 4/2017 | Gulati et al. |
| 9,615,779 B2 | 4/2017 | Pryor et al. |
| 9,636,457 B2 | 5/2017 | Newberry et al. |
| 9,735,502 B2 | 8/2017 | Stevens et al. |
| 9,735,893 B1 | 8/2017 | Aleksov et al. |
| 9,820,691 B2 | 11/2017 | Kiani |
| 9,833,152 B2 | 12/2017 | Kiani et al. |
| 9,931,065 B2 | 4/2018 | Pryor et al. |
| 9,967,040 B2 | 5/2018 | Aleksov et al. |
| 10,137,245 B2 | 11/2018 | Melker et al. |
| 10,278,732 B2 | 5/2019 | Schoonmaker et al. |
| 10,279,106 B1 | 5/2019 | Cook et al. |
| 10,398,320 B2 | 9/2019 | Kiani et al. |
| 2002/0001530 A1 | 1/2002 | Doi et al. |
| 2002/0091358 A1 | 7/2002 | Klitmose |
| 2004/0064088 A1 | 4/2004 | Gorman et al. |
| 2004/0082920 A1 | 4/2004 | Mori et al. |
| 2004/0158207 A1 | 8/2004 | Hunn et al. |
| 2005/0043687 A1 | 2/2005 | Mogensen et al. |
| 2005/0101912 A1 | 5/2005 | Faust et al. |
| 2005/0124936 A1 | 6/2005 | Mogensen et al. |
| 2005/0277887 A1 | 12/2005 | Douglas et al. |
| 2007/0060874 A1 | 3/2007 | Nesbitt et al. |
| 2007/0219496 A1 | 9/2007 | Kamen et al. |
| 2008/0091175 A1 | 4/2008 | Frikart et al. |
| 2008/0097289 A1 | 4/2008 | Steil et al. |
| 2009/0118667 A1 | 5/2009 | Haueter et al. |
| 2009/0177146 A1 | 7/2009 | Nesbitt et al. |
| 2010/0004598 A1 | 1/2010 | Eberhart et al. |
| 2010/0017141 A1 | 1/2010 | Campbell et al. |
| 2010/0064236 A1 | 3/2010 | Buck et al. |
| 2010/0064257 A1 | 3/2010 | Buck et al. |
| 2010/0077198 A1 | 3/2010 | Buck et al. |
| 2010/0082167 A1 | 4/2010 | Haueter et al. |
| 2010/0106082 A1 | 4/2010 | Zhou |
| 2010/0174239 A1 | 7/2010 | Yodfat et al. |
| 2010/0211011 A1 | 8/2010 | Haar |
| 2010/0228226 A1 | 9/2010 | Nielsen |
| 2011/0054439 A1 | 3/2011 | Yodfat et al. |
| 2011/0137297 A1 | 6/2011 | Kiani et al. |
| 2011/0152769 A1 | 6/2011 | Ramey et al. |
| 2011/0218495 A1 | 9/2011 | Remde |
| 2012/0059348 A1 | 3/2012 | Haueter et al. |
| 2012/0093311 A1 | 4/2012 | Nierzwick et al. |
| 2012/0093315 A1 | 4/2012 | Nierzwick et al. |
| 2012/0095393 A1 | 4/2012 | Reinke et al. |
| 2012/0150144 A1 | 6/2012 | Campbell et al. |
| 2012/0157655 A1 | 6/2012 | Yoneda et al. |
| 2012/0220939 A1 | 8/2012 | Yodfat et al. |
| 2012/0226124 A1 | 9/2012 | Blomquist |
| 2012/0232485 A1 | 9/2012 | Blomquist |
| 2012/0232486 A1 | 9/2012 | Blomquist |
| 2012/0232521 A1 | 9/2012 | Blomquist |
| 2012/0239362 A1 | 9/2012 | Blomquist |
| 2012/0302991 A1 | 11/2012 | Blomquist et al. |
| 2013/0041342 A1 | 2/2013 | Bernini et al. |
| 2013/0060105 A1 | 3/2013 | Shah et al. |
| 2013/0079709 A1 | 3/2013 | Eberhart et al. |
| 2013/0267811 A1 | 10/2013 | Pryor et al. |
| 2014/0128839 A1 | 5/2014 | DilAnni et al. |
| 2014/0148762 A1 | 5/2014 | Haueter et al. |
| 2014/0249500 A1 | 9/2014 | Estes |
| 2014/0276419 A1 | 9/2014 | Rosinko et al. |
| 2014/0276420 A1 | 9/2014 | Rosinko |
| 2014/0276574 A1 | 9/2014 | Saint |
| 2014/0378898 A1 | 12/2014 | Rosinko |
| 2015/0073337 A1 | 3/2015 | Saint et al. |
| 2015/0182695 A1 | 7/2015 | Rosinko |
| 2015/0182697 A1* | 7/2015 | Panzer ................ F04B 43/12 604/67 |
| 2016/0030669 A1 | 2/2016 | Harris et al. |
| 2016/0106910 A1 | 4/2016 | Yap et al. |
| 2016/0228641 A1 | 8/2016 | Gescheit et al. |
| 2016/0243302 A1 | 8/2016 | Gyrn |
| 2016/0254952 A1 | 9/2016 | Harvey et al. |
| 2016/0339172 A1 | 11/2016 | Michaud et al. |
| 2017/0014572 A1* | 1/2017 | Newberry ........... A61M 5/1723 |
| 2017/0027523 A1* | 2/2017 | Venkatraman ....... A61B 5/1123 |
| 2017/0112534 A1 | 4/2017 | Schoonmaker et al. |
| 2017/0188911 A1 | 7/2017 | Halac et al. |
| 2017/0238805 A1* | 8/2017 | Addison .............. A61B 5/7203 |
| 2017/0259015 A1* | 9/2017 | Caspers ................ A61M 5/20 |
| 2017/0274146 A1 | 9/2017 | Newberry et al. |
| 2017/0368258 A1 | 12/2017 | Fleischer |
| 2018/0060520 A1 | 3/2018 | Degen et al. |
| 2018/0339102 A1 | 11/2018 | Barraud et al. |
| 2019/0001055 A1 | 1/2019 | Gyrn |
| 2019/0184072 A1* | 6/2019 | Madden ................ F04B 43/12 |
| 2020/0037891 A1 | 2/2020 | Kiani et al. |
| 2020/0101219 A1* | 4/2020 | Wang ................ A61M 5/1723 |
| 2021/0162119 A1 | 6/2021 | Barraud et al. |

FOREIGN PATENT DOCUMENTS

| | | | |
|---|---|---|---|
| EP | 1410814 A2 | 4/2004 |
| EP | 1716879 A1 | 11/2006 |
| EP | 1944150 A1 | 7/2008 |
| EP | 2698178 A2 | 2/2014 |
| GB | 2065789 A | 7/1981 |
| WO | WO-8001934 A1 | 9/1980 |
| WO | WO-0220073 A2 | 3/2002 |
| WO | WO-2005016534 A1 | 2/2005 |
| WO | WO-2008155377 A1 | 12/2008 |
| WO | WO-2017085624 A1 | 5/2017 |
| WO | WO-2017205816 A1 | 11/2017 |
| WO | WO-2019110839 A1 | 6/2019 |

OTHER PUBLICATIONS

Accu-Check Solo, User's Manual, Accu-Check Solo micropump system, Roche Diabetes Care (2019).

Medtronic MiniMed (tm) 770G, System User Guide, https://www.medtronicdiabetes.com/sites/default/files/library/download-library/user-guides/MiniMed_770G_System_User_Guide.pdf (2020).

Omnipod-Insulin Management System, UST400 User Guide, https://www.omnipo.com/sites/default/files/2021-04/Omnipod-System_User-Guide_English (Apr. 2021).

T:slim Insulin Pump, User Guide, Tandem Diabetes Care, https://www.tandemdiabetes.com/docs/default-source/product-documents/tslim-insulin-pump (2017).

* cited by examiner

INSULIN PATCH PUMP HAVING PHOTOPLETHYSMOGRAPHY MODULE

I. FIELD OF THE INVENTION

This invention relates generally to the wearable insulin pumps having a patch-style form factor for adhesion to a user's body surface, and more particularly to an insulin patch pump having a photoplethysmography module for sensing a user's heart rate and/or other physiologic parameters.

II. BACKGROUND OF THE INVENTION

Wearable insulin pumps are known for providing a Type I Diabetes Mellitus patient with periodic bolus infusions of insulin to control the patient's blood glucose level within a desired range. Some such insulin pumps are coupled to an adhesive patch that permits the pump to be directly adhered to a user's body surface, for example the abdomen, and are referred to as "patch pumps." In addition, some previously known systems were configured to interface wirelessly with a continuous glucose monitor, which typically also may be disposed on a patch designed to be adhered to the user's body. Other previously known systems employ still further modules designed to monitor user activity and report that activity to a controller associated with the patch pump to titrate the insulin delivery in accordance with the user's activity level.

For example, U.S. Pat. No. 7,879,026 describes an infusion pump that is designed to be wearable, e.g., on a user's belt, and is coupled to an infusion cannula that extends through and is fixed to a user's skin using an adhesive patch. The infusion pump may include an accelerometer or other motion sensor to detect the user's activity level, the output of which may be used to automatically adjust a rate of dispensation of insulin to the user based at least in part on the detected movement activities of the user. The patent does not describe patch-based insulin pump nor use of a plethysmographic sensor to detect movement to control operation of such a pump.

U.S. Pat. No. 9,636,457 describes an integrated drug delivery and biosensor system that may be disposed on a patch or armband, wherein the biosensor monitors absorption of medication into the epidermis of the skin and also monitors concentration of the medication in the user's arterial blood flow. The patent describes that the biosensor system employ a photoplethysmography (PPG) circuit configured to obtain the concentration levels of medication in the user's arterial blood flow, as well as detect blood oxygen saturation, heart rate and blood pressure. That patent does not provide mechanical solutions to filter out the effects of cross-contamination of light impinging upon the PPG circuit detector element.

U.S. Pat. No. 9,735,893 describes a patch system for in-situ therapeutic treatment wherein a plurality of biological parameter monitoring devices may be disposed on separate stretchable patches designed to adhere to a user's skin. The monitoring devices communicate with each other, and other therapeutic devices, via short-range wireless, such as Bluetooth. The patent describes that patch-based monitoring devices may be configured to communicate to a belt-worn insulin pump, and that one patch-based monitoring device may include pulse oximetry electronics for measuring blood volume. The patent does not describe a patch-based insulin pump and requires intercommunication between its various components, providing a potential failure mode.

U.S. Patent Application Publication No. US 2018/0339102, assigned to the assignee of the instant application, describes a self-contained patch pump having a motor-actuated syringe together with a microdosing pump chamber. The infusion pump described in the application provides reliable and highly reproducible long-term drug infusion capability, but does not describe any on-board physiologic sensors.

U.S. Pat. No. 4,934,372 describes a standalone pulse oximeter that includes frequency domain software for determining blood oxygen saturation and heart rate in the presence of motion artifact. Similarly, U.S. Pat. No. 7,315,753 describes a method of determining heart rate and blood oxygen saturation in the presence of motion artifact, for use in standalone pulse oximeters, using Kalman filters.

In view of the foregoing drawbacks of previously known systems, there exists a need for a patch pump that includes self-contained circuitry for secondary factors that impact blood glucose level, such as physical activity determined by measuring heart rate, and which circuitry uses that indicator of physical activity to adjust dosing of insulin.

It further would be desirable to have an insulin delivery system with an integrated plethysmographic module that overcomes the drawbacks of previously known systems, and includes the ability to read through motion.

It further would be desirable to have an insulin delivery system with an integrated photo-plethysmographic module that is configured to reduce cross talk between the light emitting diodes and the detector of the module.

III. BRIEF DESCRIPTION OF THE DRAWINGS

IV. SUMMARY OF THE INVENTION

In view of the foregoing drawbacks of the previously known systems, the present invention is directed to an insulin delivery pump, in a patch form factor that can be applied to a user's body surface, and includes an integral plethysmographic module for determining physical activity. In accordance with one aspect of the invention, the plethysmographic module employs a photo-plethysmographic multi-chip package and is configured to maintain contact with the user's body surface during motion, while also reducing cross talk between the emitters and detectors and from ambient light impinging upon the plethysmographic module.

In one preferred embodiment, the multi-chip package is housed in a skin contact element that urges the plethysmographic module into contact with a skin surface of a wearer. IN one preferred embodiment, the skin contact element includes a frame having a protruding portion surrounded by a light-blocking rib. The protruding portion extends above the patient-facing exterior of the insulin delivery pump case and extends through an opening in the adhesive patch. In this way the frame is urged against and maintains contact with the skin of the user's body surface even when the user is active, thereby reducing the introduction of motion artifact into the heart rate signal determined by the plethysmographic module.

In accordance with another aspect of the invention, the insulin delivery pump includes on-board controller for processing the signals generated by the plethysmographic module to determine a user's heart rate, and for adjusting delivery of insulin from the pump responsive to the measured heart rate. The software employed by the on-board controller for processing the signals generated by the plethysmographic module illustratively may employ a frequency domain analysis, for example, as described in U.S. Pat. No. 4,934,372, or Kalman filter approach, as described in U.S. Pat. No. 7,315,753, the entireties of which are incorporated herein by reference, to reduce the motion artifact in the photoplethysmographic signals.

V. DETAILED DESCRIPTION OF THE PREFERRED EMBODIMENTS

Figure 1:
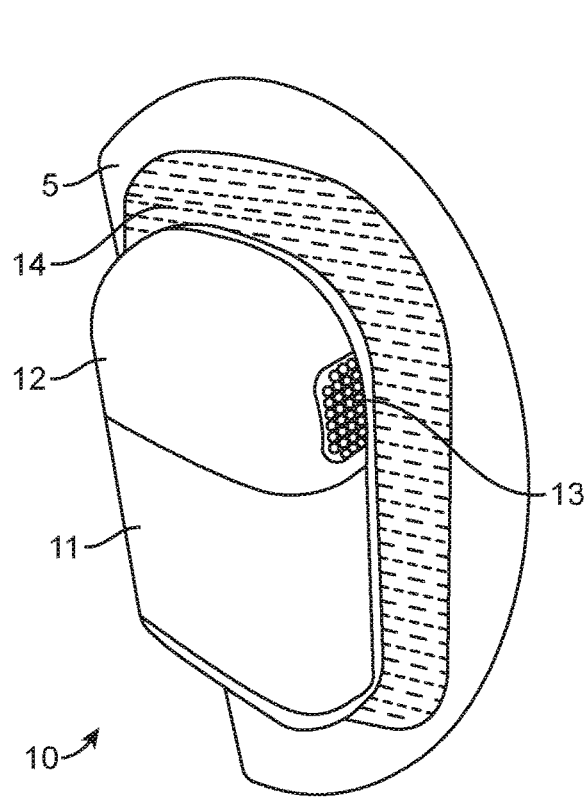
FIG. 1 is an illustrative perspective view of an insulin delivery patch pump having an integrated plethysmographic module, in accordance with the present invention, adhered to a body surface of a user.

Referring to FIG. 1, exemplary patch pump 10 having integrated photoplethysmographic module constructed in accordance with the principles of the present invention is described. In this disclosure, exemplary patch pump 10 is configured to infuse measured amounts of insulin from an on-board reservoir into a user's subcutaneous tissue via transcutaneous needles. As depicted in FIG. 1, patch pump illustratively includes exterior case 11 having removable cap 12 and button 13 that enables the user to removably attach the exterior case to breathable, preferably stretchable adhesive patch 14 that adheres to a user's body surface skin S, e.g., such as a wearer's arm or abdomen. Illustratively, patch pump 10 is configured to deliver insulin for treatment of Type I Diabetes Mellitus, although the inventive system advantageously could be employed to deliver other medications.

In accordance with one aspect of the invention, photoplethysmography is employed to determine heart rate as indicative of a wearer's physical activity, which physical activity level then is assessed to adjust the amount of insulin provided by patch pump 10. For example, using physical activity level, or a determination that the wearer is sleeping or awake, a small change may be made in an algorithm that controls an amount or rate of insulin injection, which could significantly influence blood glucose level. As described herein, the patch pump controller could use heart rate determined by the photoplethysmographic module to implement a sport mode, for example, that permits a slightly higher glucose target to decrease the risk of hypoglycemia after physical exertion.

Figure 2:
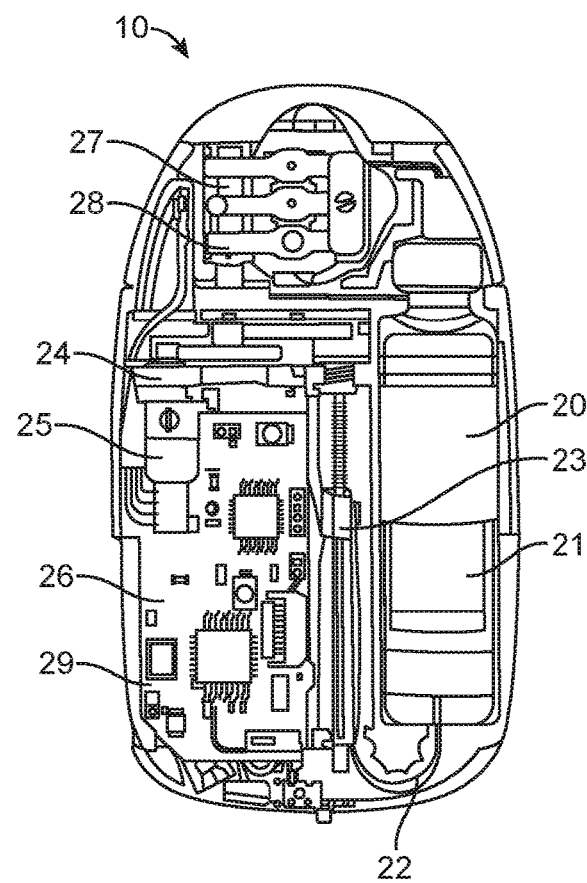
FIG. 2 is an illustrative schematic depicting the interior of the insulin delivery pump of the embodiment of FIG. 1.

FIG. 2 is a plan view of the internal components of patch pump 10 with an upper portion of exterior case 11 removed. Patch pump internal components preferably are arranged as described in commonly assigned U.S. Patent Application Publication No. US 2018/0339102, which is incorporated herein by reference. More specifically, patch pump 10 includes replaceable single-use cartridge 20 having plunger 21 coupled to actuator 22 and drive screw 23. Drive screw 23 is coupled to gear system 24 and is driven by battery-driven motor 25 under the control of controller 26. Gear system 24 also is coupled to micro-dosing unit 27, which is operated by three cam-driven levers 28. As described in the above-incorporated patent publication, medication ejected from reservoir 20 into microdosing unit 27 is infused into the user by sequential operation of levers 28. Doses of medication are delivered to the user responsive to operation of controller 26, in accordance with programming stored in memory associated with controller 26 or specifically when requested by the user, e.g., using a suitable wireless application on the user's smartphone. Controller 26 includes multiple electronic components affixed to main circuit board 29, including at least a processor, memory, wireless transceiver and battery. In accordance with the principles of the present invention, controller 26 also may include electronics for processing the output of a photoplethysmography module to determine a user's activity level, including heart rate, blood oxygen saturation, and other physiologic parameters, which may be processed to adjust the insulin delivery rate or amount to control the wearer's blood glucose level.

Figure 3:
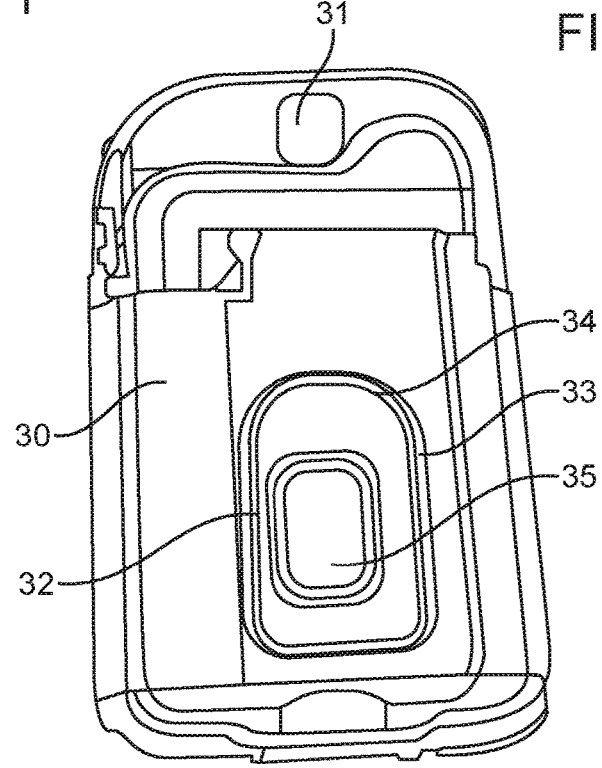
FIG. 3 is an illustrative perspective view of a prototype of the patient-facing side of the insulin delivery pump of the present invention, with the adhesive patch removed.

Referring to FIG. 3, an illustrative mock-up of patient-facing side 30 of exterior case 11 of patch pump 10 is described. Patient-facing side 30 is adhered to adhesive patch 14 and includes aperture 31 through which a transcutaneous infusion needle (not shown) exits exterior case 11. Side 30 includes raised light-blocking rib 32, having an approximately rectangular shape 33 with a semi-circular top 34, that mates with a similarly shaped opening in adhesive patch 14. Rib 32 surrounds bump 35 that projects from side 30 above the height of rib 32. As detailed below, bump 35 houses the photoplethysmography module LEDs and detectors. Rib 32 reduces ambient light from impinging on the detectors of the photoplethysmography module, while bump 35 projects from side 30 of exterior case 30 a predetermined distance to ensure that photoplethysmography module remains in contact with the user's skin during body motion.

Figure 4A:
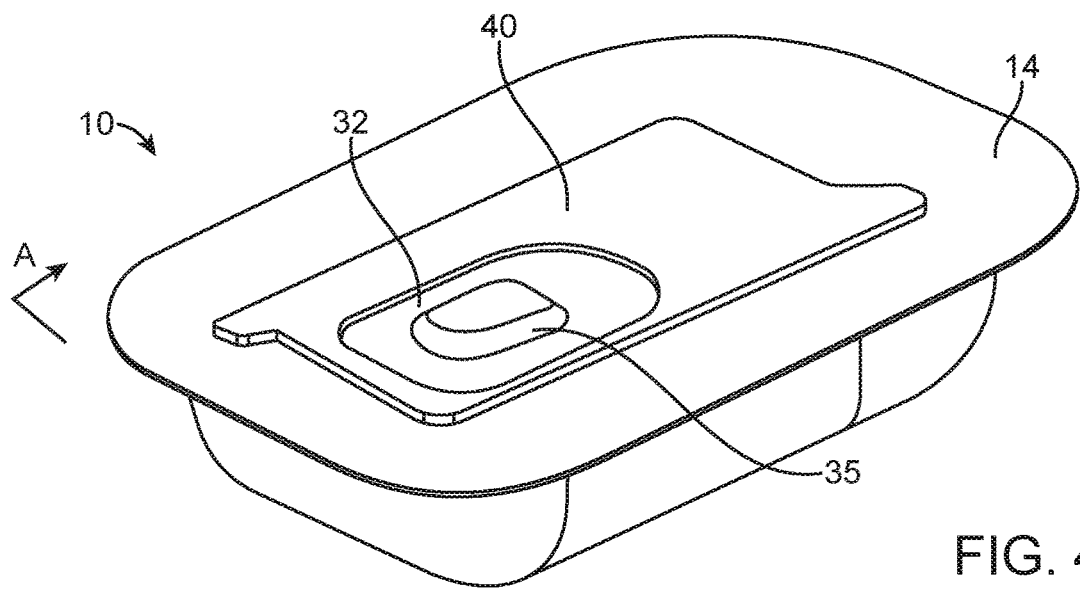
FIGS. 4A and 4B are, respectively, a perspective view of the patient-facing side of the insulin delivery pump of the present invention with the adhesive patch present and an end view of the device.
Figure 4B:
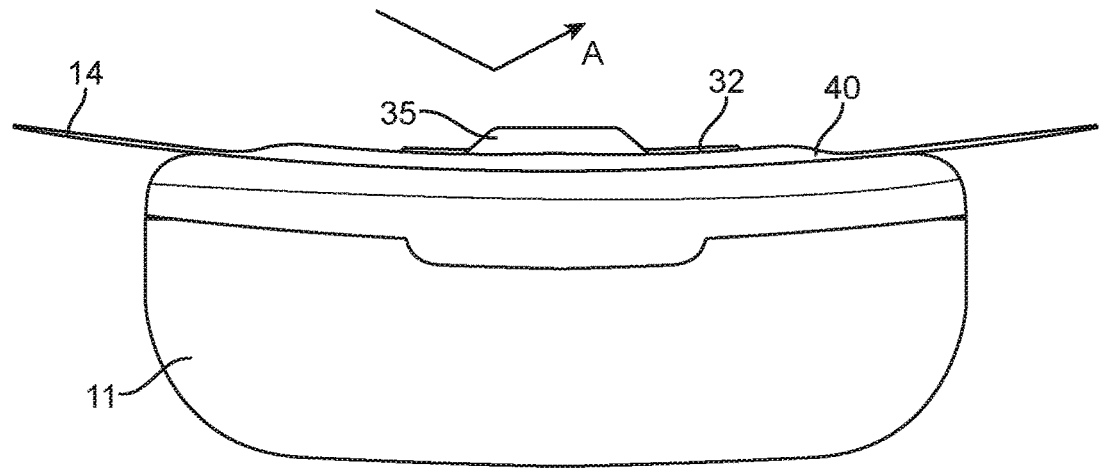

Referring now to FIGS. 4A and 4B, location of the photoplethysmography module of patch pump 10 relative to adhesive patch 14 is described. In particular, FIG. 4A is a perspective view of the patient-facing side of adhesive patch 14, showing embossment 40, raised rib 32, and bump 35, while FIG. 4B is an end view of patch pump 10 taken along view line A-A. As depicted in FIGS. 4A and 4B, patient-facing surface 30 of exterior case 11 generally includes a slight concavity. Adhesive patch 14 affixed to side 30 includes opening 41 through which the area encompassed by rib 32 protrudes from side 30 to contact a user's skin. Embossment 40 establishes a first plane above which light-blocking rib 32 extends to surround bump 35. Bump 35 extends above the surface of embossment 40 so that when adhesive patch 14 is applied to a user's body surface, the bump remains in continuous contact with a user's skin during motion. Bump 35 preferably protrudes above the surface of embossment 40 from about 0.6 mm to 2 mm, which height is selected to maintain contact of bump 35 with the user's skin while ensuring that the contact force of bump 35 does not apply excessive pressure to the skin or cause tissue necrosis.

Figure 5:
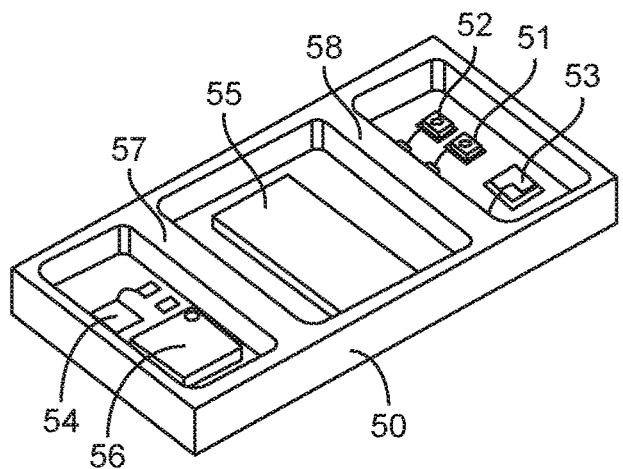
FIG. 5 is a perspective view of a multi-chip package suitable for implementing the plethysmographic module of the integrated insulin delivery pump of the present invention.

FIG. 5 depicts illustrative multi-chip photoplethysmography package 50 suitable for use in the integrated patch pump of the present invention, for example, the SFH 7072 BIOFY® Sensor device available from OSRAM Opto Semiconductors GmbH, Regensburg, Germany. PPG package 50 is to generate a strong photoplethysmography signal suitable for heart rate monitoring and pulse oximetry, and includes red LED 51, infrared LED 52, green LEDs 53 and 54, infrared cut detector 55 to detect reflected light from green LEDs 53 and 54 and broadband detector 56 to detect reflected light from red LED 51 and infrared LED 52. In one preferred embodiment, the red LED has a centroid wavelength of 655 nm, the infrared LED has a centroid wavelength of 940 nm and the green LEDs have a centroid wavelength of 530 nm. The LEDs and detectors are set in a ceramic package that includes light barriers 57 and 58 to reduce optical crosstalk between the LEDs and detectors.

As is well known in the photoplethysmography art, green LEDs are commonly used in monitoring heart rate in wearables in view of their good signal-to-noise ratio and resistance to motion artifact, while the combination of red and infrared LEDs for accurately monitoring blood oxygen saturation. Suitable algorithms are known in the art for processing photoplethysmographic signals generated with red and infrared LEDs and green LEDs to reduce the effects of motion noise, including frequency domain analysis and Kalman filter analysis techniques. Alternatively, the infrared-red LEDs may be used, instead of the green LEDs, to compute heart rates for wearers having darker skin complexions. PPG package 50 of FIG. 5 is intended to be illustrative, and more or fewer LEDs advantageously could be employed in the plethysmographic module of the present invention.

Figure 6A:
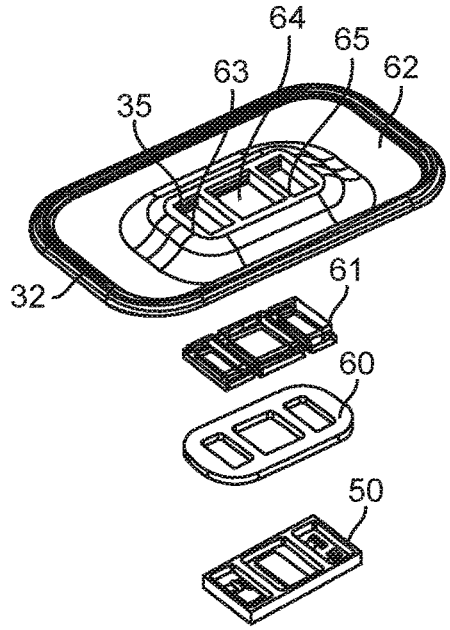
FIGS. 6A and 6B are, respectively, an exploded perspective view and a side sectional view of the plethysmographic module of the present invention including the multi-chip package of FIG. 5.
Figure 6B:
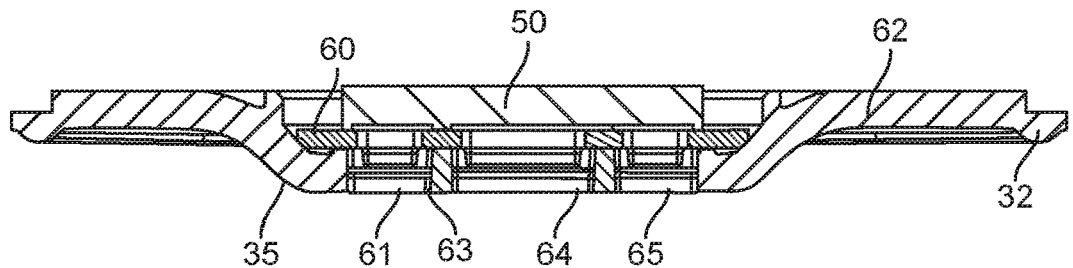

In accordance with one aspect of the invention, PPG package 50 is assembled together with layer 60 and transparent window 61 into frame 62 which forms bump 35 of FIGS. 4A and 4B, as depicted in FIGS. 6A and 6B. Frame 62 preferably comprises a sturdy biocompatible plastic or rubber material that may be formed, e.g., by overmolding on window 61, to create integral rib 32 and bump 35 having openings 63, 64 and 65. Transparent window 61 may consist of a clear plastic material having low absorptivity for light at the wavelengths of the LEDs of PPG package 50, and is designed to mate with the overmolded openings of frame 62 to provide a smooth exterior surface for bump 35. Layer 60 preferably is a closed cell foam or similar compressible material against which PPG package 50 is urged against layer 60 into contact with transparent window 61. Layer 60 and frame 62 preferably are matte black to reduce light scattering of light reflected from tissue through window 61.

Figure 7:
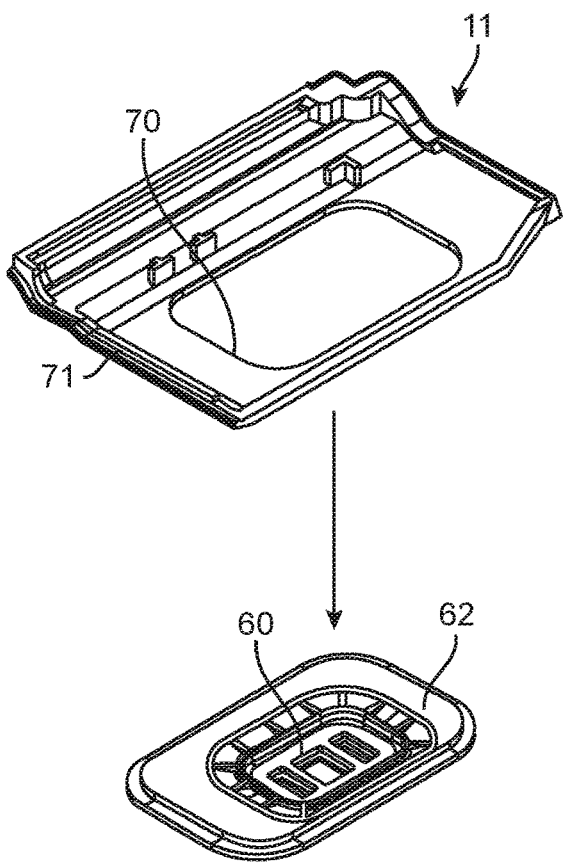
FIG. 7 is a perspective view illustrating assembly of the plethysmographic module with the patient-facing surface of the exterior case of the insulin delivery pump of the present invention.
Figure 8:
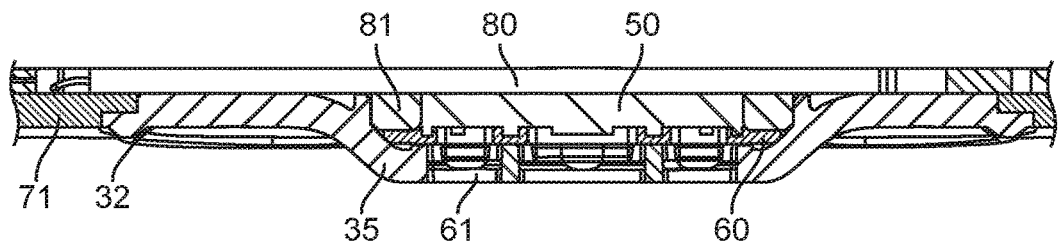
FIG. 8 is a side sectional view on the plethysmographic module assembled with the patient-facing surface of the exterior case of the insulin delivery pump.

In FIG. 7, assembly of frame 62 together, layer 60 and window 61 with exterior case 11 of patch pump 10 is described. Once frame 62 is overmolded on window 61, layer 60 may be glued in place. That assembly then is mated with opening 70 in exterior wall 71 of exterior case 11, and laser welded around its perimeter to affix the frame within opening 70. PPG package 50, with its electrical components electrically coupled to printed circuit board 80, then is assembled, along with spacer 8, as depicted in FIG. 8. Spacer 81 retains PPG package 50 in alignment with window 61 in frame 62. Printed circuit board 80 preferably is electrically coupled to main circuit board 29 of controller 26, e.g., via a flex circuit, to provide signals that permit calculation of heart rate and/or blood oxygen saturation. Circuit board 80 or main circuit board 29 additionally may have an accelerometer to determine the orientation of the user's body, e.g., upright or supine, to assess whether the user is active, resting or asleep.

In accordance with the principles of the present invention, heart rate signals generated by the on-board plethysmography module are used by controller 26 to modulate infusion of insulin from patch pump 10. In a preferred embodiment, the plethysmography module periodically measures the wearer's heart rate, e.g., once every minute, 2½ minutes or five minutes, and computes a heart rate and a quality measure for the computed heart rate. The quality measure may be used to determine whether to adjust insulin delivery to better maintain the stability of the wearer's blood glucose level.

In addition, the heart rate data may be used to compute an activity intensity level, similar to that employed in physical activity monitors, such as resting, passive behavior, and low, medium and high levels. Such an activity level could be used to adjust parameters of the insult delivery algorithm to permit a "sport mode" that adjusts insulin delivery to reduce the risk of hypoglycemia during, and especially after, engaging in vigorous or sports activities. The heart rate also could be evaluated to determine whether the wearer is asleep or awake. For example, when a wearer is asleep, the parameters of the infusion algorithm used in controller 26 could be switched to a sleep mode. This sleep mode may allow fine-tuning of the wearer's glucose level to allow provide better sleep well and improve time in a targeted glucose range. Such adjustments are expected to be possible because while sleeping, the wearer does not eat, is not physically active and is not physically or emotionally stressed.

Determination that a wearer is asleep or awake additionally could be based on, or confirmed by, data from the on-board accelerometer discussed above. Accelerometer outputs also could be analyzed to assess where patch pump 10 is being worn by the user, and to determine body orientation. The sleep/wake information also may be analyzed to provide a quality measure of the measurement, and thus allow the infusion algorithm employed by the controller to have a good degree of confidence regarding its insulin delivery adjustments.

The output of the on-board plethysmographic module also may be used to validate that patch pump 10 is adequately adhered to the wearer's skin to allow insulin injection. If, for example, patch pump 10 includes a capacitive circuit for continuously detecting that the pump is adhered to a wearer's skin, the plethysmographic module could provide confirmation that the pump is located on the wearer's skin.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention.

What is claimed:
1. A medication infusion device comprising:
   a flexible adhesive patch configured to be removably attached to a wearer's skin, the flexible adhesive patch including an opening;
   a pump having a pump case with a lower surface configured to contact the flexible adhesive patch, the pump case configured to be removably coupled to the flexible adhesive patch to transcutaneously deliver doses of medication from a replaceable single-use cartridge dis- posed within the pump case to the wearer, the pump case including an embossment on the lower surface; and a photoplethysmographic module disposed to extend through the embossment, the photoplethysmographic module having an LED, a detector and a skin contact element including at least one transparent window, wherein the LED emits light to and the detector receives reflected light from, the wearer's skin through the at least one transparent window, wherein the skin contact element protrudes from the embossment and is configured to extend through the opening of the flexible adhesive patch, wherein the flexible adhesive patch is configured to conform to the embossment, and the embossment and the skin contact element together are configured to apply pressure to the wearer's skin sufficient to retain the photoplethysmographic module in contact with the wearer's skin during motion without causing skin or tissue necrosis.

2. The medication infusion device of claim 1, wherein the skin contact element includes a contact surface having a matte finish.

3. The medication infusion device of claim 2, wherein the contact surface is surrounded by a light-blocking rib.

4. The medication infusion device of claim 1, wherein the pump further comprises a controller programmed to analyze signals output by the photoplethysmographic module to adjust an algorithm that controls delivery of medication to the wearer.

5. The medication infusion device of claim 4, wherein the controller is disposed on a main circuit board and the photoplethysmographic module is electrically coupled to the main circuit board by a flex circuit.

6. The medication infusion device of claim 4, further comprising an accelerometer disposed within the pump case and electrically coupled to the controller.

7. The medication infusion device of claim 1, wherein the pump case includes a gear system and micro-dosing unit.

8. The medication infusion device of claim 7, wherein the micro-dosing unit includes cam-driven levers.

9. The medication infusion device of claim 1, wherein the skin contact element comprises a frame that is overmolded onto the at least one transparent window.

10. The medication infusion device of claim 1, wherein the replaceable single-use cartridge is removably disposed within the pump case.

11. An insulin delivery device comprising:
an adhesive patch configured to be removably attached to a wearer's skin, the adhesive patch including an opening;

a pump configured to be removably coupled to the adhesive patch to transcutaneously deliver insulin from an on-board replaceable single-use cartridge to the wearer, the pump having a pump case including a lower surface with an embossment configured to contact the adhesive patch so that the adhesive patch conforms to the embossment; and a plethysmographic module disposed within the pump case, the plethysmographic module having an LED, a detector and skin contact element including at least one transparent window, wherein the LED emits light to and the detector receives reflected light from, a skin surface of the wearer via the at least one transparent window, wherein the skin contact element protrudes from the embossment and is configured to extend through the opening of the adhesive patch, and the embossment and the skin contact element together are configured to apply pressure to the wearer's skin sufficient to retain the plethysmographic module in contact with the wearer's skin during motion without causing skin or tissue necrosis.

12. The insulin delivery device of claim 11, wherein the skin contact element includes a contact surface having a matte finish.

13. The insulin delivery device of claim 12, wherein the contact surface is surrounded by a light-blocking rib.

14. The insulin delivery device of claim 11, wherein the pump further comprises a controller programmed to analyze signals output by the plethysmographic module to adjust an algorithm controlling delivery of insulin to the wearer.

15. The insulin delivery device of claim 14, wherein the controller is disposed on a main circuit board and the plethysmographic module is electrically coupled to the main circuit board by a flex circuit.

16. The insulin delivery device of claim 14, further comprising an accelerometer disposed within the pump case and electrically coupled to the controller.

17. The insulin delivery device of claim 11, wherein the pump further comprises a gear system and a micro-dosing unit.

18. The insulin delivery device of claim 17, wherein the micro-dosing unit include cam-driven levers.

19. The insulin delivery device of claim 18, wherein the single-use cartridge is coupled to the micro-dosing unit.

20. The insulin delivery device of claim 11, wherein the skin contact element comprises a frame that is overmolded onto the at least one transparent window.

* * * * *